(12) United States Patent
Folkers

(10) Patent No.: US 9,078,416 B2
(45) Date of Patent: Jul. 14, 2015

(54) DETECTION SYSTEM

(75) Inventor: Christianus Johannes Folkers, Havelock North (NZ)

(73) Assignee: Cament Limited, Te Awamutu (NZ)

( * ) Notice: Subject to any disclaimer, the term of this patent is extended or adjusted under 35 U.S.C. 154(b) by 114 days.

(21) Appl. No.: 13/701,875

(22) PCT Filed: Jun. 3, 2011

(86) PCT No.: PCT/NZ2011/000097
§ 371 (c)(1),
(2), (4) Date: Dec. 4, 2012

(87) PCT Pub. No.: WO2011/152739
PCT Pub. Date: Dec. 8, 2011

(65) Prior Publication Data
US 2013/0096369 A1    Apr. 18, 2013

(30) Foreign Application Priority Data

Jun. 4, 2010 (NZ) .................................. 585936
Dec. 14, 2010 (NZ) ................................. 589903

(51) Int. Cl.
*A01K 29/00* (2006.01)
*A61B 17/425* (2006.01)
(Continued)

(52) U.S. Cl.
CPC ............. *A01K 29/005* (2013.01); *A01K 11/00* (2013.01); *A01K 11/006* (2013.01); *A61B 17/425* (2013.01); *G06K 19/07327* (2013.01); *G06K 19/07749* (2013.01)

(58) Field of Classification Search
CPC ..... A61D 17/00; A61D 19/00; A61D 17/004; A01K 11/006; A01K 29/005; A61B 10/0012; A61B 2503/40; G06K 19/067; G06K 7/0008; G07C 9/00111; Y10S 128/903; Y10S 224/901

USPC .................... 600/33; 40/300–304; 119/174
See application file for complete search history.

(56) References Cited

U.S. PATENT DOCUMENTS 4,895,165 A * 1/1990 Blair ........................... 600/551
5,566,679 A   10/1996 Herriott
(Continued)

FOREIGN PATENT DOCUMENTS

EP    0657098    6/1995
GB    2139117    11/1984
(Continued)

OTHER PUBLICATIONS

Athina Nickitas-Etienne; International Preliminary Report on Patentability from PCT/NZ2011/000097; The International Bureau of WIPO; Geneva, Switzerland; Dec. 4, 2012; 6 pages.
(Continued)

*Primary Examiner* — Christine H Matthews
*Assistant Examiner* — Joshua D Lannu
(74) *Attorney, Agent, or Firm* — Florek & Endres PLLC

(57) ABSTRACT

A detection tag and apparatus for the detection of the reproductive status of animals, or for assisting in the drafting of selected animals. The detection tag is capable of electronically transmitting a signal. Tags for detecting the reproductive status of an animal have a first surface that is affixable to the hide of an animal and a second and opposite surface which includes abradable material. Such detection tags are configured such that removal of some or all of the abradable material alters the ability of the detection tag to transmit a signal electronically or alters a characteristic of the electronically transmitted signal. A tag reader is used to read the signal from the tag. The detection tag can include an RF/EMF blocking circuit/loop and/or removable flood coat layer which is damaged/removed partially or completely during mounting of the animal allowing the tag to indicate a status change.

20 Claims, 9 Drawing Sheets

(51) Int. Cl.
*A01K 11/00* (2006.01)
*G06K 19/073* (2006.01)
*G06K 19/077* (2006.01)

(56) References Cited

U.S. PATENT DOCUMENTS

| | | | |
|---|---|---|---|
| 6,236,318 | B1 | 5/2001 | Yang et al. |
| 6,427,627 | B1 * | 8/2002 | Huisma ............... 119/51.02 |
| 6,467,430 | B1 | 10/2002 | Stampe |
| 6,708,648 | B2 | 3/2004 | Stampe |
| 6,925,417 | B2 | 8/2005 | Sasaguri |
| 7,137,359 | B1 | 11/2006 | Braden |
| 7,230,535 | B2 | 6/2007 | Jackson et al. |
| 7,277,016 | B2 * | 10/2007 | Moskowitz et al. ...... 340/572.3 |
| 7,724,136 | B2 | 5/2010 | Posamentier |
| 2005/0242950 | A1 * | 11/2005 | Lindsay et al. ......... 340/539.26 |
| 2007/0063895 | A1 * | 3/2007 | August et al. ................. 342/359 |
| 2007/0103316 | A1 * | 5/2007 | Tuttle ........................ 340/572.8 |
| 2008/0084309 | A1 * | 4/2008 | Posamentier ............. 340/572.7 |
| 2008/0110406 | A1 | 5/2008 | Anderson et al. |
| 2008/0128486 | A1 * | 6/2008 | Lowe ........................... 235/376 |
| 2008/0186186 | A1 | 8/2008 | Campbell |

FOREIGN PATENT DOCUMENTS

| | | |
|---|---|---|
| NZ | 528756 | 10/2006 |
| NZ | 564384 | 11/2009 |

OTHER PUBLICATIONS

Brochure from EstrusAlert at http://www.estrusalert.com; 2012; 1 page.

Soosa Gnanasingham; International Search Report from PCT/NZ2011/000097; Australian Patent Office; Woden, Act, Australia; Oct. 11, 2011; 3 pages.

Soosa Gnanasingham; Written Opinion from PCT/NZ2011/000097; Australian Patent Office; Woden, Act, Australia; Oct. 11, 2011; 5 pages.

* cited by examiner

DETECTION SYSTEM

FIELD OF THE INVENTION

The invention relates to an improved detection system. More particularly it relates to an improved detection system for detecting the reproductive state of animals, or for detecting animals that have been selected for a particular reason.

BACKGROUND OF INVENTION

The detection of the reproductive status of animals is highly desirable for farmers. It is especially desirable for a farmer to know when individual cows in a herd are 'in heat'. The early detection of cows in heat allows the farmer to improve his livestock by selective breeding and to better plan his business operations. This can be achieved by mating selected animals, using artificial insemination or any other suitable method. When using any of these methods, it is necessary to determine accurately and reliably when cows are in heat so that the cows in heat could be singled out and inseminated. The heat cycle of cows is active only for a short period of time and hence detection and insemination must be done within this period.

Various methods have been used in the prior art for the detection of cows 'in heat'. The most common method of detection used is visual observation where the cows seen to allow mounting by other cows are separated from the herd by a farmer. However the farmer must quickly identify and mark the cows in heat since the heat cycle of the cows only lasts for a short period of time as mentioned above. This may be difficult in a large herd as cows are generally widely dispersed and 24 hour observation may be impossible. Therefore this method is time consuming and also the heat cycle of most cows may go undetected.

Another frequently used method of detection involves the application of paint on the tail-bone of a cow, where the subsequent smudging of this paint indicates that the cow was mounted by another animal. This method involves a skilled farmer closely observing each animal in order to detect which animals have been mounted and hence it is also very time consuming and is not very reliable in harsh weather conditions.

An alternative method is to use indicators on the backs or rumps of cows that are set off when other animals mount the cows in heat. In most cases, these methods incorporate some form of visual indicator such as a reflective device/tag that becomes exposed when mounting occurs or some sort of fluid reservoir that becomes discharged when mounting occurs. This means that the indicators still require some form of visual observation and interpretation by a skilled farmer in order to identify the animals in heat and hence the heat cycles of some animals of a large herd may still be missed due to delays in checking.

Furthermore complicated systems incorporating image capture devices and software that interpret images using various algorithms have been developed so that the observation and interpretation of the indicators/tags are fully automated. However these 'automated visual detection systems' have some external requirements in order to function properly, such as suitable lighting conditions, exact positioning and 'line of sight' view for image capturing. Furthermore they include hardware that are expensive (digital cameras, computers, lighting systems, etc), are sensitive to fouling, dust or dirt and include software interpretation modules that are inherently difficult to develop to an accepted state of reliability. Also, the indicators/tags used in these systems, frequently get covered in manure and other dirt which makes visual image processing error prone. Therefore a system which is completely insensitive to these types of disadvantages is required.

In the prior art, once the cows 'in heat' have been identified, they are separated from the herd (referred to as 'drafting') for further treatment e.g.: artificial insemination. This drafting process is done either manually by a farm-worker handling a gate or at various levels of automated drafting by automatically switching a gate when the cow concerned is present. Usually the drafting process is done during or after milking of the cow when the cow leaves the milking parlour through the exit race.

According to current farming practice, drafting is carried out using a three step process. The first step involves a skilled worker identifying the cows through visual identification. The second step involves manual or automated marking of cows. Manual marking of cows is done with, for example, shaving cream. In an automated system a cow ID is entered into a computer program instead of marking the cow with shaving cream. Typically this marking is done on cows when they enter the milking shed/platform.

The third step of drafting is carried out while the cows are exiting the milking platform by switching one or more gates. In the case of manual selection, a gate operator operates the gate when a marked cow (i.e.: a cow having shaving cream on its back) is seen at the gate entrance. In the case of automated selection, the system reads the cow ID when the cows are in the exit race (using a tag reader of a prior art animal identification system—e.g.: RFID ear-tags used for identification of cows). After reading the cows ID the automated system checks if the read cow ID was previously entered into the computer in step two and operates the gate accordingly.

The above described manual and automated methods of drafting have disadvantages similar to the methods used for detection of 'heat' in animals. For example manual visual drafting may not be accurate in a farm with a large herd of animals and automated drafting require expensive hardware and software.

In other situations, animals may be selected while they are held in a stall, pen or race, for example when an inspector selects lambs that are suitable to go to the meat works. In such cases a visual mark is placed on the selected animals and those animals are drafted out manually. The operation takes a number of staff since some are required to encourage the animals through the drafting gates, while another controls the gates.

OBJECT OF THE INVENTION

It is an object of the invention to provide an improved detection system that ameliorates some of the disadvantages and limitations of the known art or at least provide the public with a useful choice.

SUMMARY OF INVENTION

In a first aspect the invention resides in a detection tag for the detection of the reproductive status of animals, the detection tag being capable of electronically transmitting a signal, and the detection tag having a first surface that is affixable to the hide of an animal and having a second and opposite surface which includes abradable material, and the detection tag is configured such that removal of some or all of the abradable material alters the ability of the detection tag to transmit a signal electronically or alters a characteristic of the electronically transmitted signal.

Preferably the abradable material is a removable flood coat layer, and removal of the flood coat layer of the second surface of the detection tag allows or disallows the electronic transmission of status information from the detection tag.

Preferably the abradable material includes a conductive circuit and the detection tag is configured such that partial or complete removal of the conductive circuit, or breaking of the conductive circuit, allows the electronic transmission of status information from the detection tag.

Preferably the conductive circuit of the detection tag is configured such that it is damaged or broken partially or completely when the animal is mounted by another animal.

Preferably the conductive circuit is an RF/EMF blocking circuit/loop, circular or otherwise, made from: aluminium foil, conductive paint, liquid conductive material, or any other conductive material; and the circuit/loop shields electronic components of the detection tag from RF/EMF energy by forming an inductive loop.

Preferably the abradable material forms, or is at least a part of, an antenna of the detection tag.

Preferably the detection tag is normally inactive and is activated only when the abradable material is partially or completely removed.

Preferably the detection tag incorporates a 'Radio Frequency Identification' (RFID), or an 'Electronic Article Surveillance' (EAS), electronic circuit or microchip.

Preferably the RFID circuit/chip uses low or high frequency radio frequency (RF) communication and the EAS circuit/chip uses radio frequency (RF), magnetic (magneto-harmonic), acousto-magnetic (magnetostrictive) or microwave communication.

Preferably the flood coat layer covers part or all of an antenna of the detection tag.

Preferably the removal of part or all of the flood coat layer alters the strength and/or frequency of the signal from the detection tag.

Preferably the flood coat layer includes a layer of conductive material or RF/EMF shielding or absorbing material.

Preferably the flood coat layer includes a plurality of layers, and at least one of the layers is a layer of RF/EMF shielding/blocking material and at least one of the layers is a layer of latex material.

Preferably the altered characteristic of the electronically transmitted signal is a change in the frequency range within which the detection tag becomes readable.

Preferably the detection tag is thicker in the regions of the tag covered by the abradable material.

Preferably the detection tag includes an adhesive layer on the first surface.

Preferably the detection tag is substantially bone-shaped.

In a second aspect the invention resides in an apparatus for detecting of the reproductive status of an animal, wherein the apparatus includes at least one detection tag substantially as described herein and at least one tag reading device and/or interpretation module which is configured to interpret the signal from the detection tag.

In a third aspect the invention resides in a method of detecting the reproductive state of an animal wherein the method comprises the steps of:
  affixing a detection tag substantially as described herein onto a female animal,
  allowing the animal to mingle with animals of the same type for a period of time,
  passing the animal by a detection tag reading device or taking the detection tag reading device to the animal, and
  evaluating the signal, or absence of a signal, from the detection tag, and making a determination as to reproductive state of the animal.

In a further aspect the invention resides in an apparatus for the detection of the reproductive status of animals, the apparatus comprising at least one detection tag, at least one tag reader and at least one interpretation module, wherein the tag reader reads status information from the tag and the interpretation module interprets status information read by the tag reader, wherein a first surface of the detection tag is affixed to an animal and the second surface of the detection tag is coated with a removable flood coat layer and wherein removal of the flood coat layer of the second surface of the detection tag allows or disallows the reading of status information from the detection tag by the tag reader.

In a further aspect the invention resides in an apparatus for the detection of the reproductive status of animals, the apparatus comprising at least one detection tag, at least one tag reader and at least one interpretation module, wherein the tag reader reads status information from the tag and the interpretation module interprets status information read by the tag reader, wherein a first surface of the detection tag is affixed to an animal and the second surface of the detection tag includes a conductive circuit and wherein partially or completely damaging or breaking of the conductive circuit, allows the reading of status information from the detection tag by the tag reader.

Preferably the conductive circuit of the detection tag is damaged or broken partially or completely when the animal is mounted one or more times by another animal.

Preferably the detection tag is normally inactive and is activated only when the conductive circuit is partially or completely damaged or broken during mounting, thus allowing reading of status information by the tag reader.

In a further aspect the invention resides in an apparatus for the detection of the reproductive status of animals, the apparatus comprising at least one detection tag affixed to at least one animal, at least one tag reader and at least one interpretation module, wherein the tag reader is capable of reading status information from the detection tag and the interpretation module interprets status information read by the tag reader, wherein the detection tag is altered when the animal is mounted, such that it allows or disallows the tag reader to read status information from the detection tag.

Preferably the alteration of the detection tag includes damaging or breaking, partially or completely, of a conductive circuit of the detection tag, the removal of a flood coat layer of the detection tag or the complete detachment of the detection tag from the animal.

Preferably the conductive circuit is an RF/EMF blocking circuit/loop, circular or otherwise, made from aluminium foil, conductive paint, liquid conductive material, or any other conductive material, where the circuit/loop shields the detection tag from RF/EMF energy by forming an inductive loop and when the circuit/loop is damaged or broken partially or completely, the RF/EMF energy field is no longer shielded, absorbed or dissipated and the detection tag becomes readable/detectable.

Preferably the detection tag is bone-shaped to maximise the attachment area of the detection tag on the animal.

Preferably the tag is affixed on an animal with an adhesive layer of the tag, the adhesive layer being a water resistant, heat-resistant (for example up to 70 degrees Celsius), solvent based aerosol contact adhesive such as, for example, 'Selleys kwik grip spray'.

Preferably the adhesive layer is sprayed on the attachment surface of the tag and the skin of the animal prior to attachment, for example, approximately 5 minutes prior to attachment especially when attaching on animals with wet fur.

Preferably the detection tag has tapered edges to prevent the tag from being detached from the animal during mounting.

Preferably the detection tag is made thicker at the centre, for example, approximately 2 mm thick, in order create a separation between the tag and the skin of the animal which improves the detection rate of the tag.

Preferably the interpretation module is a software program on a computer.

Preferably reading status information from the detection tag corresponds to reading the operational status of the detection tag in the form of binary status indicator such as, for example, '0' for a non-operational tag and '1' for an operational tag.

Preferably the detection tag is attached to the rump or back of an animal.

Preferably the flood coat layer of the detection tag, affixed to an animal is designed such that the flood coat is removed by friction when the animal is mounted by another animal.

Preferably the flood coat layer of the detection tag is used to provide visual confirmation of mounting of the animal, to a farmer, as indicated by the detection apparatus.

Preferably the detection tag and the tag reader incorporate non-visual forms of detection such as RFID or 'Electronic Article Surveillance' (EAS) detection.

Preferably the detection tag is an electronic detection tag such as for example an RFID or EAS tag and the tag reader is an electronic tag reader.

Preferably the electronic detection tag and the electronic tag reader is a low or high frequency RFID tag/reader or an EAS tag/reader.

Preferably the EAS tag and the EAS tag reader uses radio frequency (RF), magnetic (magneto-harmonic), acousto-magnetic (magnetostrictive) or microwave communication.

Preferably the flood coat layer covers an antenna of the detection tag.

Preferably the removal of the flood coat layer exposes the antenna of the detection tag allowing the detection tag to be read by the tag reader.

Preferably the flood coat layer is a solid layer of conductive, RF/EMF shielding or absorbing material in the form of a coat of paint mixed with ferrite powder or other metallic powders or flakes or a liquid conductive material in the form of a fluid filled tube or a bladder.

Preferably the flood coat layer consists in one or more sub layers where a sub-layer of RF/EMF shielding/blocking paint is covered (or 'sandwiched') by one or more sub-layers of scratchy (latex) material on the top and/or the bottom surface of the RF/EMF shielding/blocking sub layer.

In a further aspect the invention resides in an apparatus for the detection of the reproductive status of animals, the apparatus comprising at least one detection tag, at least one tag reader and at least one interpretation module, wherein the tag reader reads status information from the tag and the interpretation module interprets status information read by the tag reader, wherein a first surface of the detection tag is affixed to an animal and the second surface of the detection tag is coated with a removable flood coat layer and wherein when the flood coat layer is removed from second surface of the detection tag, the information of the detection tag read by the tag reader is altered.

In a further aspect the invention resides in an apparatus for the detection of the reproductive status of animals, the apparatus comprising at least one detection tag, at least one tag reader and at least one interpretation module, wherein the tag reader reads status information from the tag and the interpretation module interprets status information read by the tag reader, wherein a first surface of the detection tag is affixed to an animal and the second surface of the detection tag is covered with a conductive RF/EMF shielding liquid filled tube or bladder and wherein when the liquid filled tube or bladder is dispersed within the detection tag, the information of the detection tag read by the tag reader is altered.

Preferably the alteration of information in the detection tag is achieved by a change of the frequency-range within which the detection tag becomes readable, by changing the power input needed for a microchip of the detection tag, by changing signal output strength or by any other method as herein defined.

In a further aspect the invention resides in a method of detecting the reproductive state of animals wherein the method comprises the steps of:
  affixing an detection tag onto a female animal, the detection tag having a removable flood coat layer on a first surface,
  the removable flood coat layer being removed from the detection tag upon another animal mounting the female animal,
  the detection tag modifying its operational status as a result of having the flood coat layer removed and,
  the modified operational status of the detection tag being read by a tag reader indicating that the female animal with the affixed tag is 'in heat'.

In a further aspect the invention resides in a method of detecting the reproductive state of animals wherein the method comprises the steps of:
  affixing a detection tag onto a female animal, the detection tag having a conductive RF/EMF shielding liquid filled tube or bladder attached on one surface,
  the liquid filled tube or bladder being dispersed within the detection tag upon another animal mounting the female animal,
  the detection tag modifying its operational status as a result of having the liquid filled tube or bladder dispersed and,
  the modified operational status of the detection tag being read by a tag reader indicating that the female animal with the affixed tag is 'in heat'.

In a further aspect the invention resides in a method of drafting animals wherein the method comprises the steps of:
  affixing at least one tag to at least one animal identified as having at least one particular status or condition,
  at least one tag reader reading status information from the tag(s) affixed to the animal(s),
  at least one interpretation module interpreting the status information read by the tag reader and outputting one or more indication signals,
  the indication signals allowing the animal(s) to be drafted to a correct location.

Preferably the indication signals are visual, audible and/or other types of signals and include one or more electronic signals which are used for automated drafting of an animal(s).

Preferably in an automated drafting system, the animal(s) is drafted to the correct location automatically by an automated drafting system based on the indication signal(s) provided by the interpretation module.

Alternatively in a manual drafting system, the animal(s) is drafted to the correct location, by a drafting gate operator, based on the indication signal(s) provided by the interpretation module.

Preferably the at least one particular status or condition of the animal(s) includes conditions (or statuses) such as illness, for example, mastitis, lameness, or other animal illnesses, the animal(s) being under or over a particular age, of a particular breed or any other criteria, lactation status of cows, body condition score, body fat score (particularly of sheep), or a group of animals needing to be moved to a different location, herd or farm.

Preferably the tag is an 'always-active' electronic tag such as 'always-active' RFID tag (that is not blocked by any layer or ring or other methods described) or an electronic detection tag such as an RFID detection tag or an EAS detection tag.

In a further aspect the invention resides in an apparatus for the detection of at least one status or condition of at least one animal, the apparatus comprising at least one tag attached to the animal(s), at least one tag reader and at least one interpretation module, wherein the tag reader reads status information from the tag and the interpretation module interprets status information read by the tag reader and outputs one or more indication signals.

Preferably the indication signals are visual, audible or other types of signals and include one or more electronic signals which are used for automated drafting of an animal(s).

Preferably the at least one status or condition of the animal(s) includes conditions (or statuses) such as illness, for example, mastitis, lameness, or other animal illnesses, the animal(s) being under or over a particular age, of a particular breed or any other criteria, lactation status of cows, body condition score, body fat score (particularly of sheep), or a group of animals needing to be moved to a different location, herd or farm.

Preferably the tag is an 'always-active' electronic tag such as, for example, an 'always-active' RFID tag or an electronic detection tag such as an RFID detection tag or an EAS detection tag.

Preferably the indication signal(s) provided by the interpretation module allows the concerned animal(s) to be automatically or manually drafted towards a group of animals with similar status or conditions.

Preferably the drafting is done manually by a skilled farm worker or automatically by an automated drafting system.

Preferably the tag is a sticker type tag, clip-on tag, Velcro type tag, a necklace or a tag having any other method of attachment to animal(s) and it can be attached to any body part of the animal(s) e.g.: to the wool of a sheep, to the hide of a cow, or strapped to the leg or neck of an animal.

Preferably the apparatus is used for the detection of at least one status or condition of any animal(s) such as, for example, cow, bull, sheep, poultry, etc.

This invention may also be said to consist in the parts, elements and features referred to or indicated in the specification of the application, individually or collectively, and any or all collectively of any two or more of the parts, elements or features, and where specific integers are mentioned herein which have known equivalents such equivalents are deemed to be incorporated herein as if individually set forth.

DESCRIPTION

These and other aspects, which should be considered in all its novel aspects, will become apparent from the following description, which will be given by way of example only with reference to the accompanying drawings, in which:

FIG. 1 is a block diagram showing the general principle of the invention in accordance with a first preferred embodiment of the invention.

FIG. 2*a* is a diagram showing a detection tag prior to applying the flood coat layer or the circuit/loop of conductive material.

FIG. 2*b* is a diagram showing a detection tag with the RF blocking flood coat layer applied.

FIG. 2*c* is a diagram showing a detection tag with the RF blocking flood coat layer removed.

Figure 5A:
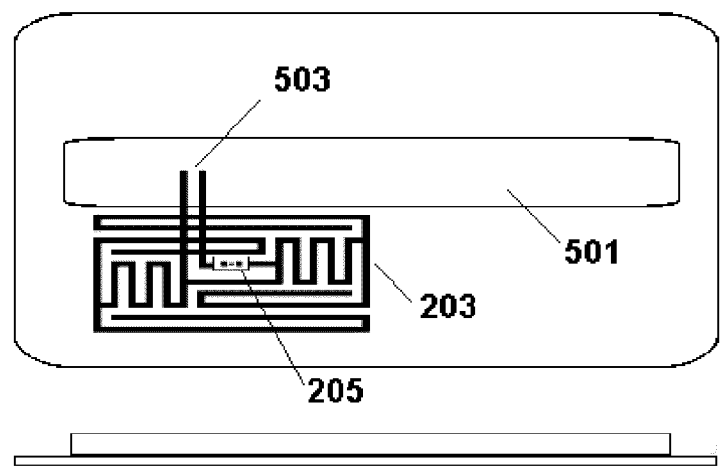
Figure 5B:
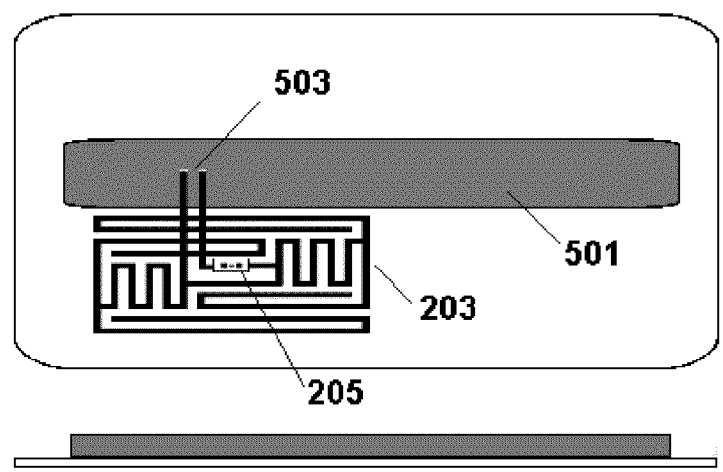

FIG. 5*a-b* are diagrams showing an alternative version of detection tags having a conductive fluid filled tube.

Figure 6A:
Figure 6B:
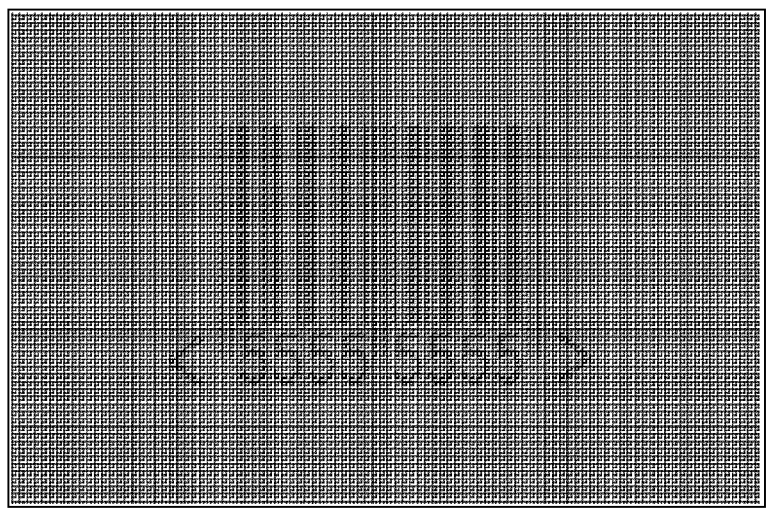
Figure 6C:

FIG. 6*a-c* are diagrams showing barcode detection tags in accordance with an alternative embodiment of the invention.

Figure 7A:
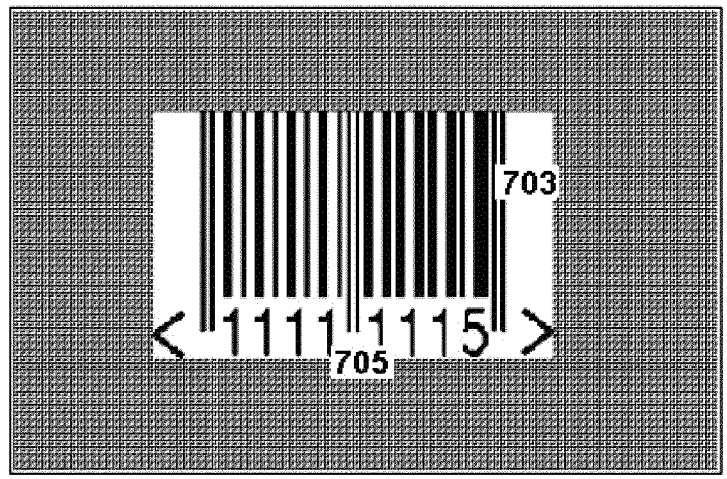
Figure 7B:
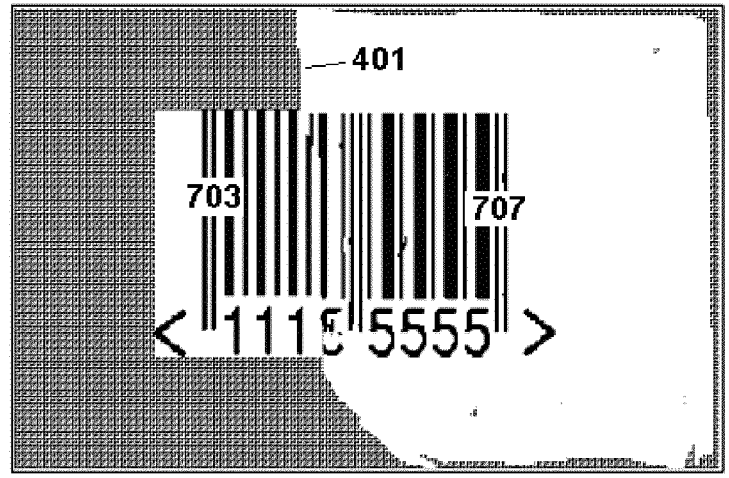

FIG. 7*a-b* are diagrams showing barcode detection tags with multiple printed barcodes in accordance with a further alternative embodiment of the invention.

DESCRIPTION OF PREFERRED EMBODIMENTS

The following description will describe the invention in relation to preferred embodiments of the invention, namely an improved detection system. The invention is in no way limited to these preferred embodiments as they are purely to exemplify the invention only and that possible variations and modifications would be readily apparent without departing from the scope of the invention.

Figure 1:
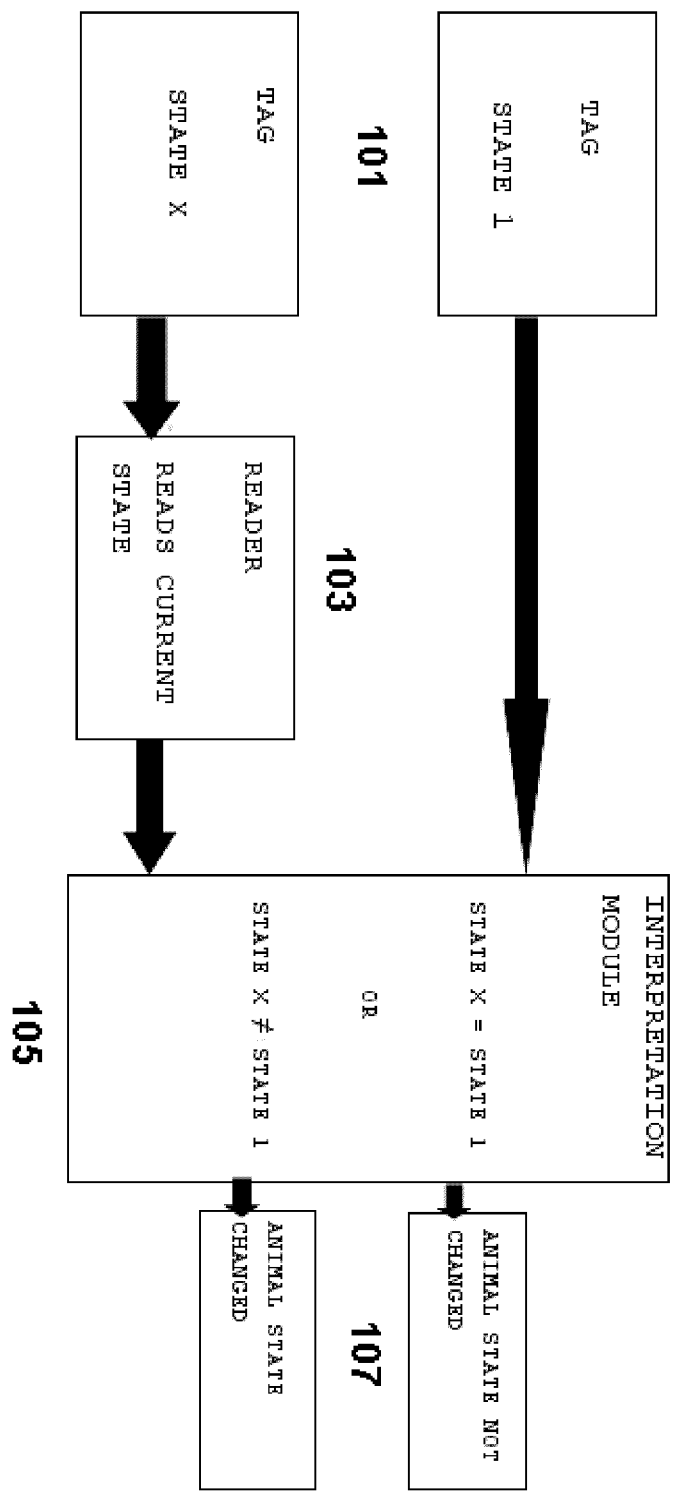

FIG. 1 shows the general principle on which the invention functions. The invention involves detecting (or identifying) of a specific state of a detection tag 101 (also referred to as an identification tag—see definition later in the specification) attached to an animal using a tag reader 103 (also referred to as a tag reading device). The tag reader reads an electronically transmitted signal(s) of the tag which indicates the current state of the tag. The current state (STATE X) of the tag is then compared to a previously known state (STATE 1) through an interpretation module 105. The interpretation module then determines if the current state of the detection tag is changed from the previous state (i.e.: If STATE X=STATE 1 or STATE X≠STATE 1) and therefore determining whether the animal has been mounted 107.

The detection system disclosed in this invention is intended to be used alongside existing animal identification systems (i.e.: used in addition to existing animal identification systems). For example, the tag reader 103 may be triggered to operate by an external trigger such as an additional tag reader that is used for identifying the ID number/mark of a specific animal, indicating that the animal is within range and ready for inspection. The tag reader 103 then attempts to read the electronically transmitted signal(s) of the detection tag 101 affixed to the animal and depending on the type of detection system used, it would detect 1) the absence of an electronically transmitted signal, or 2) the presence of an electronically transmitted signal, and/or 3) the specific ID read and/or 4) the frequency that allowed a successful read, and/or 5) the signal strength. This information is then processed by the interpretation module 105 to determine the reproductive state of the animal and this state is preferably stored in a database together with the unique cow ID of that particular animal (as identified from a separate animal identification system). Hence the detection system and the detection tags of this invention are not intended to be used for the purpose of identification of animals but rather identification of a particular state or condition of the animals.

The detection tag 101 is preferably a non-visual detection tag such as, for example, an RFID tag or an EAS detection tag. However in alternative embodiments of the invention, the detection tag 101 can also be a barcode tag or any other type of detection tag as will be explained later. In the case where an RFID tag is used as the detection tag 101, the RFID tag includes either a low or high frequency RFID circuit/microchip. Similarly when using an EAS tag as the detection tag 101, the EAS detection tag includes a radio frequency (RF) EAS circuit/microchip as will be explained later in the specification. FIGS. 2-5 show non-visual detection tags (such as RFID tags, EAS tags, etc) 201 and FIGS. 6-7 show barcode detection tags 501. The use of both tags is explained in more detail later in the specification.

A feature common to all types of detection tags described above (with the exception of the 'always-active' tags described later), is that they all include a layer of abradable material, which is for example a special blocking layer or conductive loop of removable material, on the surface of each detection tag. The special blocking layer (referred to as a 'flood coat layer' hereinafter) is similar to the coating of 'scratchy' lottery tickets. It comprises of a conductive material such as paint with ferrite powder and has RF or EMF shielding or absorption properties which prevent RF reception in the tag. When using a conductive loop as the abradable material, the loop is preferably made from an RF/EMF blocking material or an electrical conductive material such as for example, aluminium foil or conductive paint as will be described in more detail later.

Figure 3:
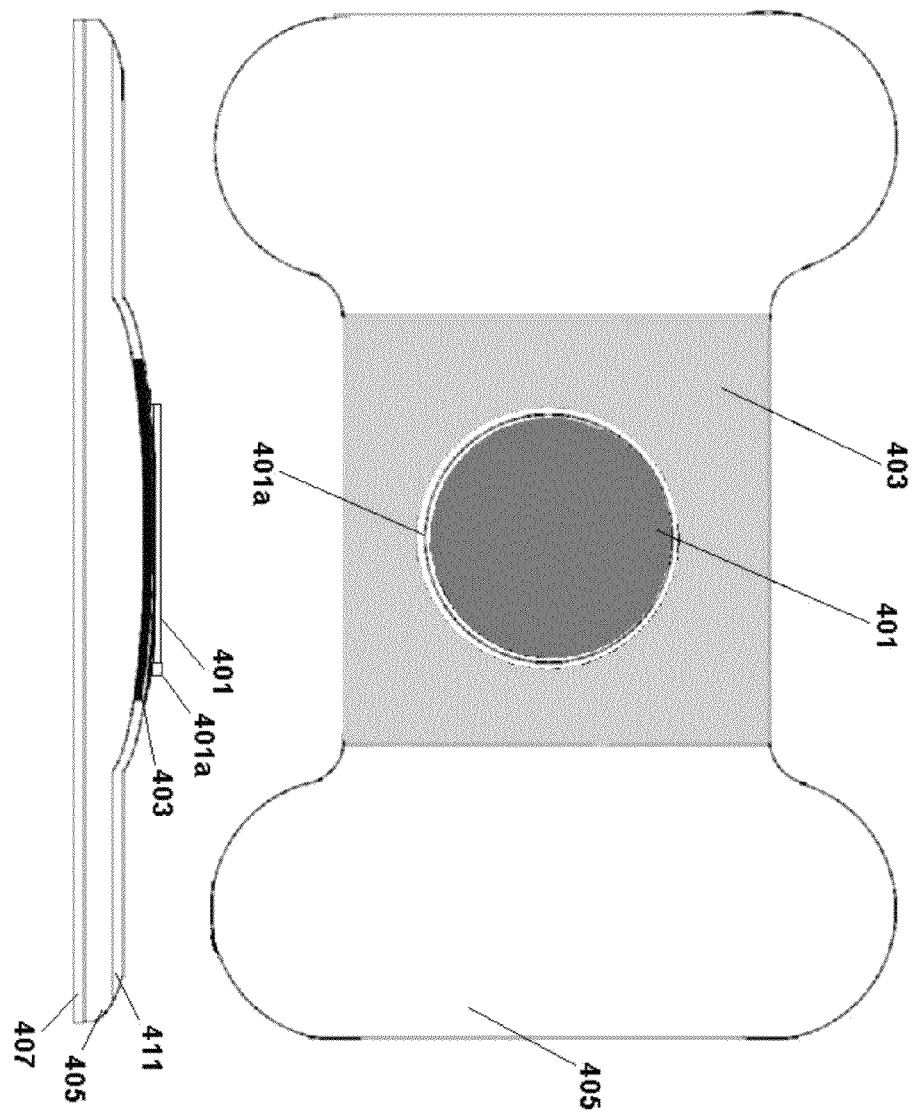
FIG. 3 is a diagram showing a bone-shaped detection tag having a conductive circuit/loop and a flood coat layer applied in accordance with a first preferred embodiment of the invention.

The detection tag 101 is preferably 'bone shaped' as shown in FIG. 3. The tag 101 is designed to be affixable to the hide of an animal (especially to the rear spinal area) and the centre portion of the tag (as indicated by 403) is designed to be placed on top of the spinal bone of the animal. The larger 'wing' areas 405 on both sides of the tag are designed to hold the centre portion firmly in place and the bone-shaped design maximises the attachment area of the tag. The design of the tag further allows the centre portion 403 to be small and flexible. However in alternative embodiments, the tag can be made to any other desired shape and size.

In the preferred embodiment of the invention shown in FIG. 3, the dimensions of the tag 101 are preferably 120×80 mm for the entire tag (including the 'wing' areas 405). The dimensions of the centre portion 403 of the tag are preferably 50×50 mm. The maximum thickness is preferably 3 mm at the centre of the tag. These dimensions are given by way of example only and other sets of dimensions can be used in alternative embodiments.

Figure 4:
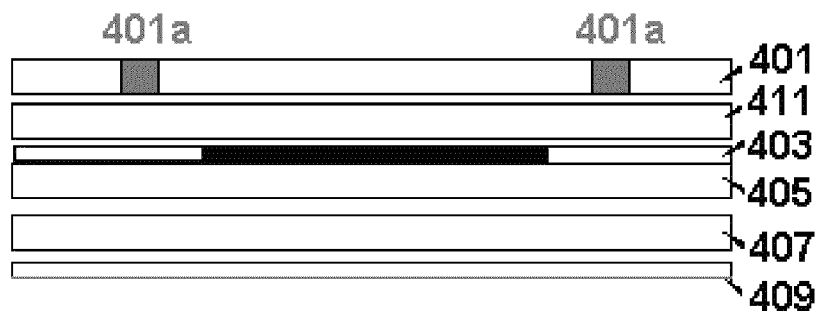
FIG. 4 is a diagram showing a cross-section view of the various different layers of the detection tag (diagram not to scale).

The detection tag 101 comprises of several layers as shown in FIGS. 3 and 4. The top-most layer is an abradable material layer such as a flood coat layer 401 and/or an RF/EMF blocking circuit/loop 401a as shown. However the flood coat layer can be omitted 401 and only the RF/EMF blocking circuit/loop 401a is used in some embodiments of the invention as detailed later. The blocking circuit/loop 401a shields the tag from RF/EMF energy, until the circuit/loop is broken or damaged at one or more places. The RF/EMF blocking circuit/loop 401a is preferably an aluminium ring (made from, for example, thin aluminium 'sticker material) which is glued on top of the centre of the tag (or a self adhesive type aluminium ring) as shown. Alternatively the aluminium ring can be inserted into a special pocket or sleeve (or ridges made from for example rubber bands) moulded onto the top of the tag. This special pocket or sleeve (not illustrated) is intended to rip or break apart during use of the tag when mounting occurs (or the ridges break) which causes the aluminium ring to be dislodged from the sleeve thus exposing the tag to RF/EMF energy.

Underneath the top-most layer is a protective layer of lamination 411. It is preferably made from a transparent (or coloured), waterproof material and can be injection moulded, hot-laminated, glued or welded to the tag to avoid delaminating during use. Its purpose is to provide protection from damage to the sensitive components of the detection tag. The material chosen for the lamination layer 411 should be supple (e.g.: rubber or silicon) and must also have a smooth surface to support the rubbing off of the flood coat layer 401 during use. A smooth surface also avoids the tearing off of the entire tag during use due to high friction. However in the case where a material that is supple, rubbery and is also smooth (i.e.: has low-friction) is not available, an additional low friction layer can be added on top of a supple, rubbery layer 411. This additional layer (not shown) is preferably a transparent polyester layer or a UV cured transparent spray coat. However other suitable low-friction materials can be used in alternative embodiments. Furthermore the protective layer 411 is tapered at the sides to decrease the chance of the tag being removed during use (i.e.: when mounting occurs) as illustrated in the side-view diagram of FIG. 3.

The actual RFID tag/EAS tag layer (or barcode tag layer) 403 having the RF/EAS circuit/microchip (or barcode) is located underneath this protective layer 411. More details of this tag layer 403 and its operation will be given in the examples described later in the specification.

The RFID/EAS tag (or barcode tag) is placed on a second protective layer 405 which is also made from a durable and weather-proof material located below the RFID/EAS tag/barcode tag layer 403 as shown. The second protective layer 405 is also made from a suitable supple, rubbery, smooth (i.e.: low friction) lamination material similar to the protective layer 411 as explained above. This second protective layer 405 and the first protective layer 411 essentially sandwiches the electronic RFID tag/EAS tag 403 in between them minimising damage to the tag during use. Furthermore the protective layer 405 is also tapered at the edges to decrease the chance of the tag being removed during use (FIG. 3). In the initial trials performed by the inventor, this layer 405 had a sub-layer of foam of approximately 2 mm thickness which allowed the electronic tag 403 to be separated from the skin of the animal by 2 mm, decreasing interference and causing the detection rate of tag to be improved. Therefore a slight separation (e.g.: 2 mm) between the tag layer 403 and the surface of the animal is important as it provides much improved read-rates for the tags during use. It should be noted that the separation between the tag and the animal can also be achieved by making the mid-section of the layer 405 thicker (e.g.: approximately 2 mm thicker in the regions covered by abradable material) as shown in the side view diagram of FIG. 3. The foam sub-layer can be omitted if the protective lamination layer 405 is made thicker in the middle as shown.

Underneath the protective layer 405 is an adhesive layer 407 which is used to attach the tag to the back or rump of an animal. It is preferably a layer of weather-proof adhesive and more details of the preferred adhesive used by the inventor are given later. Furthermore the adhesion to the animal can be greatly improved by applying an aerosol glue approximately 5 minutes prior to applying the tag. This method is especially useful when attaching the tag on animals with wet/damp fur.

The adhesive layer 407 is covered by a peel-off layer 409 (FIG. 4) which is removed when the tag is attached to an animal. In operation, when an animal affixed with a detection tag of this invention, is mounted by another animal the flood coat layer 401 and the RF/EMF blocking circuit/loop 401a is partially or fully damaged/removed by friction created by rubbing during mounting. Once the flood coat layer is removed and/or the RF/EMF blocking circuit/loop 401a is broken or damaged, as shown in FIG. 2c (RFID/EAS or other non-visual type tags) and FIG. 6c (barcode tags), the detection tag 101 is read by the tag reader 103 and interpreted by the interpretation module 105.

In the preferred embodiment described above, the flood coat layer 401 consists of one or more sub-layers (not shown). The top-most sub-layer is a scratchy layer which is similar to the latex scratchy layer of lottery tickets followed by a sub-layer of RF blocking/shielding paint. In an alternative embodiment, the flood coat layer 401 consists of a RF blocking/shielding sub-layer 'sandwiched' in between two scratchy layers, where the scratchy layers form the top and bottom sub-layers. However in further alternative embodiments, the flood coat layer 401 comprises in a single layer of paint which is both scratchy and has RF shielding/blocking properties combined or alternatively it may comprise in any number of layers providing the same properties.

In order for the tags 101 to indicate the 'in heat' status of the animals under inspection (i.e.: whether the animals have been mounted or not), the electronic transmission signals of the tags or various different characteristics of the electronically transmitted signals of the tags 101 are set to change when mounting occurs. More particularly, the detection tags are configured such that the removal of some or all of the abradable material alters the ability of the tags to transmit signals electronically or alters one or more characteristics of the electronically transmitted signals. These variations and characteristics are explained below along with details on how to implement each of them.

Non-Visual Detection Tags (RFID, EAS, etc)

Figure 2A:
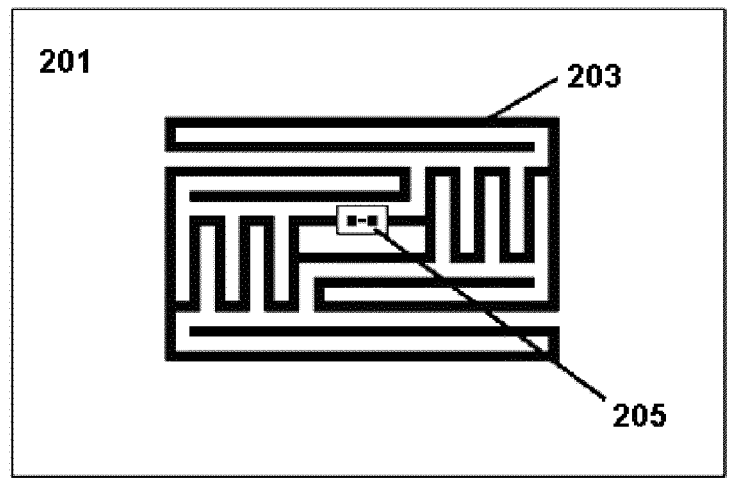
Figure 2B:
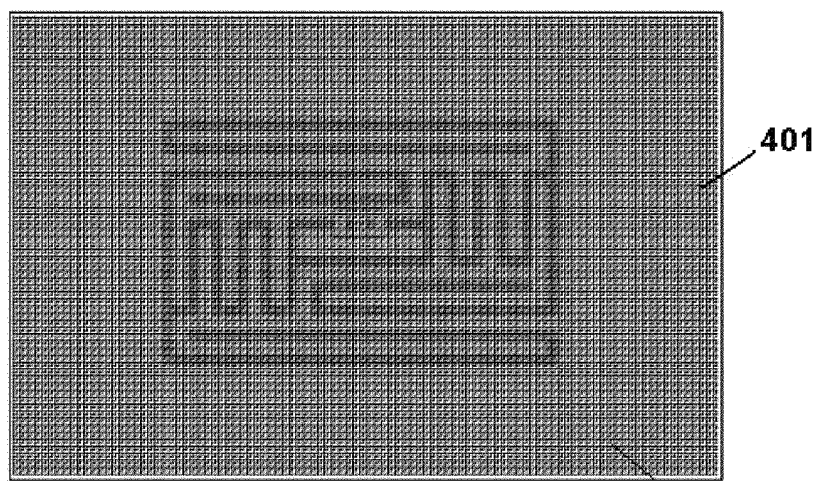
Figure 2C:
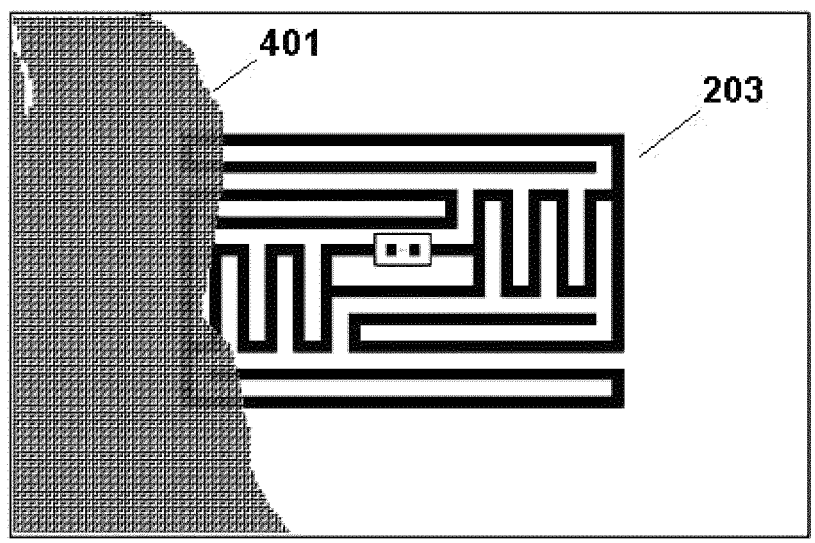

The RFID tag/EAS tag layer 403 (refer FIGS. 3 and 4) of the detection tag 201 preferably includes three main components, as illustrated in FIGS. 2a-c. They are the antenna 203, the microchip 205 (also known as an integrated circuit) and the tag layer itself 403. The tag layer can be made out of any suitable material such as plastic or rubber to ensure flexibility and durability in harsh weather. The antenna and the microchip are preferably sandwiched in between the protective lamination layers 405 and 411 of the tag. The antenna and microchip can alternatively be coated with water resistant protective layers 405 and 411 (FIGS. 3 and 4) with inert properties (as far as RF and EMF are concerned) and the layer 411 is preferably covered by a flood coat layer 401 and RF/EMF blocking circuit/loop 401a as explained before. The RF/EMF blocking circuit/loop 401a and the optional flood coat layer 401 prevents the detection tag from being read by a tag reader due to its RF/EMF shielding properties. Once it is partially or fully damaged/removed (as shown in FIG. 2c) the antenna 203 becomes exposed and the tag is read by the tag reader. Thus the status change of the detection tag is determined by the tag reader/interpretation module. The interpretation module 105 is preferably a software program on a computer with an output display indicating whether the animal state has changed or not. Preferably, the computer could be part of other automated systems frequently installed in (dairy) farms.

An alternative version of the detection tag is shown in FIGS. 5a-b. In this version, the flood coat layer is replaced with a conductive fluid filled tube 501 which forms part of the antenna circuit 503 of the detection tag as shown. The tube 501 is normally empty meaning that the tag would not transmit its status when de-active (FIG. 5a). When pressed against by an external force (i.e.: another animal mounting) a conductive fluid enters the tube (from a fluid storage within the tag, not shown) and completes the antenna circuit 503, thus activating the tag (FIG. 5b). It is also possible in alternative embodiments; to have the tube 501 normally filled with a conductive fluid which shorts out the antenna circuit 503 and when mounting occurs, the tube 501 bursts emptying it of fluid, thus allowing the tag to be activated.

The following variables of the detection tags can be used to indicate if the status of the detection tag has changed since previous scan by the tag reader.
 1. The presence or absence of an detection tag signal (Binary)
 2. The strength of the detection tag signal (Scale)
 3. The specific frequency that the detection tag is read (Binary)
 4. The strength of the tag reader's signal that is needed to successfully read the tag (Scale)
 5. The specific code returned by the tag reader based on the number of open or closed circuits (specialized tag needed as described later) (Scale)
 6. A combination of the above either in one application or by combining multiple tags.

Each of the above variables has further variables in terms of how each variation is implemented, as explained in the following examples:

EXAMPLE 1

Example 1 relates to a detection system where the presence or absence of a detection tag signal is used to determine any change of state of the detection tag. This example is a binary mode example and the detection tag can only have one of two possible states i.e.: It is either activated or deactivated. It should be noted that this example cannot distinguish between a non-functioning (that is shielded) and a missing tag.

The following options can be used to indicate a status change in a detection tag which operates as a normally deactivated system:
  The antenna 203 of the tag (FIG. 2) is covered by a removable flood coat layer 401 and/or RF/EMF blocking circuit/loop 401a. Activation occurs when the RF/EMF blocking circuit/loop 401a is broken or damaged (partially or completely) and/or the flood coat layer is removed by an external force, thus uncovering the antenna 203 of the detection tag, making the tag detectable by a tag reader.
  The power supply of the tag, where the antenna is connected to the microchip 205 is short-circuited by a conductive material. The material can be liquid or solid (e.g.: paint with ferrite powder). Activation occurs when the short-circuiting material is removed.
  The antenna 203 of the tag is disconnected from the microchip 205. When an external force is applied, a conductive liquid material closes the circuit, thus allowing the microchip to be powered and be discoverable (FIG. 5a-b).
  A special active detection tag is used, that is powered by a photo-voltaic sensor (as opposed to being powered by the inductive field of the tag reader's signal as done in passive detection tag RFID tags. This photo-voltaic sensor only provides an electric current when electromagnetic radiation (usually in the visible light spectrum) falls upon it. Activation occurs when a flood coat layer that is shielding the photo-voltaic sensor (blocking ambient light) is removed by an external force, thus uncovering the sensor and powering up the microchip of the detection tag, thus making it readable.

A special tag is used, that has a photo-resistor sensor included in the tag circuit between the antenna and the microchip. This sensor becomes more conductive when electromagnetic radiation (usually in the visible light spectrum) falls upon it. Activation occurs when a flood coat layer is removed from the sensor by an external force, thus allowing light to fall on the sensor, which becomes more conductive, thus allowing a current to pass through the circuit to power up the microchip of the detection tag.

It is important to note that the external force referred to in the above options and also in the following examples relate to the frictional force created by rubbing of two animals when a female animal (e.g.: a cow) is being mounted by a male or another female animal. In order for mounting to occur, a female animal is usually allowed to mingle with female and/or male animals of the same type for a period of time.

A detection tag can also be set to change its status from a normally activated to deactivated state to indicate mounting of an animal. The following options can be used to indicate a status change in such a detection tag which operates as a normally activated system:

- The antenna 203 of the tag is removed by an external force, thus deactivating the tag and rendering it undetectable to the reader. The antenna itself is made from a removable conductive flood coat layer of abradable material or any other type of conductive circuit/loop in this option.
- The entire detection tag 201 or vital parts of the tag (e.g.: antenna, microchip, etc) are damaged or removed completely or partially by the mounting/rubbing action thus deactivating the tag.
- The connection between the antenna 203 and the microchip 205 of the tag is broken by an external force, thus deactivating the tag and rendering it undetectable to the tag reader.
- The connection between the antenna and the microchip of the tag is short circuited by a conductive liquid material, thus deactivating the tag and rendering it undetectable to the tag reader.
- A special active detection tag is used, that is powered by a photo-voltaic sensor (as opposed to by the inductive field of the tag reader's signal). This photo-voltaic sensor only provides an electric current, when electromagnetic radiation (usually in the visible light spectrum) falls upon it. Deactivation occurs when the uncovered photo-voltaic sensor is covered with a liquid material that blocks the electromagnetic radiation (light), thus powering down the microchip of the detection tag.
- A special tag is used, that has a photo-resistor sensor included in the tag circuit between the antenna and the microchip. This sensor becomes more conductive, when electromagnetic radiation (usually in the visible light spectrum) falls upon it. Deactivation occurs when the previously uncovered sensor is covered with a liquid material that blocks the electromagnetic radiation (light), the sensor becoming less conductive and blocking a current passing through the circuit and powering down the detection tag.

Example 1 describes two types of detection tags, namely normally active tags which are deactivated by the mounting of the animal and normally deactive tags which are activated by mounting of the animal as described above. The preferred form of the detection system as described in this invention has the detection tags set to normally inactive status which are activated during mounting as described below.

The preferred form of the detection tag 101 of this invention has a RF/EMF blocking conductive circuit/loop (e.g. aluminium ring) 401a as the layer of abradable material placed on the top of the detection tag (FIG. 4). Therefore the default status of the detection tag is inactive (i.e.: cannot be detected by the tag reader). The tag is activated (i.e.: the tag is allowed to be read by the tag reader) when the abradable material of the circuit/loop 401a is damaged or broken partially or completely during mounting of the animal. The preferred tag used in this example is an EAS tag which indicates an 'on' status when activated and an 'off' status at all other times.

The normally inactive tag described above has the disadvantage that it may not be activated in the case where the entire tag is detached from the animal during mounting. Therefore the heat cycle of this particular animal may be missed due to the failure of the tag to respond with an active signal after mounting has occurred, unless a farm-worker visually inspects the animal for a missing tag. This disadvantage does not apply to normally active tags described previously as no active signal (or the lack of a tag on the animal) would indicate that a mounting has occurred.

EXAMPLE 2

Example 2 relates to a detection system where a change of strength of the detection tag signal is used to determine any change of state of the detection tag. This example works on a scale which means that the tag can indicate an infinite number of states and hence can allow for a more detailed interpretation of the status change of the tag. This example also allows for detecting a missing tag.

The following options can be used to indicate a status change in a detection tag which incorporates changing its signal strength when a status change occurs.

- The antenna 203 of the tag is partially shielded by a conductive or RF absorbent flood coat layer or an RF/EMF blocking circuit/loop. Partial damage or removal of the layer by an external force will increase the strength of the signal. The strength of the signal can thus be used to interpret the amount of layer/loop removed or still present, indicating the amount of activity that led to the current state.
- The antenna 203 of the tag is unshielded and will output a signal at the full strength. An external force will partially cover the antenna with a conductive liquid material, thus weakening the strength of the signal. The relative strength of the signal can be used as an indicator of the amount of coverage and indirectly, of the amount or frequency of the external force applied. Also no signal would indicate a missing tag.

EXAMPLE 3

Example 3 relates to a detection system where a change in the operational frequency of the tag is used to determine any change of state of the detection tag (i.e.: the altered characteristic of the electronically transmitted signal of the tag is a change in frequency range within which the tag becomes readable). This example is a binary mode example which means that the detection tag can only indicate any one of a set of predefined states i.e.: each state is at a specific frequency. This example can detect a missing tag since a signal must always be present in any state.

The following options can be used to indicate a status change in a detection tag which utilizes a frequency change to indicate a status change.

- The antenna 203 of the detection tag is shaped so that its virtual length enables coupling with the tag reader at a specific frequency range. Modifying the virtual length of the antenna changes this frequency range. The tag reader can scan through a range of predefined frequencies, in order to locate the particular frequency of the detection tag. It can be used as an indicator of the antenna shape or virtual/actual length of the antenna.

Decrease of the effective length of the antenna
- Part of the antenna is made of removable conducting flood coat layer (can be a solid as paint or a liquid in a tube or bladder). Applying an external force will remove this part, thus shortening the effective length of the antenna changing the frequency used by the tag reader to read the tag.
- The antenna is made of parts, connected by a removable material. Applying an external force, will break the circuit between the antenna parts, thus creating an antenna with a different effective length or shape, thus changing the frequency of the antenna.

Increase of the length of the antenna
- The antenna is made of parts separated by a small gap. Applying an external force, will close the circuit between the antenna parts e.g. with a conductive liquid material, thus creating an antenna with a different effective length or shape, thus changing the frequency of the antenna.

EXAMPLE 4

Example 4 relates to a detection system where a specific code is returned by the tag based on the number of covered or uncovered switches in the tag indicating any change of state of the detection tag.

The following options can be used to indicate a status change in a detection tag which utilizes a change of code returned by the tag to indicate a change of state.

A special microchip 205 is used, that can read the state of one or more micro-switches/circuits located on the tag and transmit a specific code based on the open or close state of these switches.

Opening or closing one or more switches
- The switches are normally closed by a conductive liquid/solid material. When an external force is applied the conductive material is removed from one or more of the switches, thus breaking the circuits of the switches. The detection tag returns a specific code indicating which switches are closed and which switches are opened, thus providing a means of assessing the strength and or frequency of the external force that was applied (e.g.: number of mounting times of the animal, the duration or force of mounting).
- The circuits are normally open. When an external force is applied a conductive liquid material is forced between the contacts of one or more of the switches, thus closing the circuits. The detection tag returns a specific code indicating which switches are closed and which switches are opened, thus providing a means of assessing the strength and or frequency of the external force as above.

EXAMPLE 5

Barcode Tags

This example involves reading of a specific state of a barcode tag 601 (FIG. 5) instead of using a non-visual (RFID, EAS, etc) tag 201. The general principle of operation is the same as in the previous examples where the current state of the tag is compared to a known previous state of the tag and if a change of state is determined, the animal is identified as being 'in heat'. Similar to a non-visual (RFID, EAS, etc) tag reader, a barcode tag reader is also triggered to operate by an external trigger (e.g.: an RFID reader used for identifying an animal, or any other switch, photo cell or proximity detector), indicating that an animal is within range and is ready for inspection. The tag reader then attempts to detect the detection tag 601 affixed to the animal and depending on the type of detection system used, it would detect 1) the absence of a barcode 603, 2) presence of a barcode 603, 3) the specific ID read or 4) the number and values of several barcode-id's to determine the reproductive state of the animal. The barcode tag reader defers from the non-visual (RFID, EAS, etc) tag reader since the barcode tag reader requires 'line of sight' visibility to obtain a successful scan of the tags. Therefore the animals may need to be pre-positioned or handled by humans to obtain a good read of an attached barcode in a place with sufficient ambient lighting.

Although barcode tags have a limited number of options in terms of indicating status change when compared to non-visual (RFID, EAS, etc) tags, they can also be successfully utilised for determining 'heat' of animals. For example, a detection system using a normally deactivated barcode tag attached to an animal (i.e.: with the barcode covered by a flood coat layer 401 as shown in FIG. 6*b*) (state 1), the presence of a barcode 603 and/or the successful reading of the barcode (state 2) indicates that the tag was activated by the removal of the flood coat layer 401 (FIG. 6*c*). This in turn indicates that the animal has been mounted and that it is 'in heat'. Similarly in a normally active barcode tag (state 1) where the barcode is normally readable by a reader, the absence of a readable barcode-ID would indicate that the system was activated (state 2). In this case, an opaque liquid that is released at the time of mounting which covers the barcode is used to indicate a change of state and hence mounting by another animal.

The following options of the barcode tags can be set to indicate if the status of the ID tag has changed since previous scan by the tag reader.
1. The presence or absence of a readable barcode-id (binary option, no missing tag indication possible)
2. The number of readable barcode-id's on the tag (scale, can be used to detect a missing tag where no tags are read)
3. The specific barcode ID number on the tag (binary or scale, can be used to detect a missing tag where no tags are read)
4. A combination of the above either in one application or by combining multiple tags.

FIGS. 7*a-b* show a barcode ID tag 701 as described in option 3 above. The barcode ID tag 701 has a hidden barcode 707, a flood coat layer 401 covering the barcode 707 and a second barcode 703 printed on top of the flood coat layer. In operation, the barcode ID tag is attached to the back of an animal as explained earlier. When a mounting occurs on the animal, the flood coat layer 401 is removed, in turn removing the second barcode 703 and exposing the hidden barcode 707 of the tag (FIG. 7*b*). Therefore the barcode reader, reads a different ID number when a change of state occurs and hence two specific barcode numbers are used to indicate state 1 (not 'in heat') and state 2 ('in heat'). This option also indicates a missing barcode ID tag where no barcode is read when scanned.

EXAMPLE 6

Other Uses of the Tag

As described in the background section, the current processes of manual and automated drafting of animals have some disadvantages. In this example, the detection system of the current invention, is integrated into or replaces various parts of the drafting process overcoming those disadvantages as detailed below.

The lowest level implementation of having the detection system integrated into the drafting process involves placing the tag reader 103 on the exit race of a milking parlour. When a cow is picked up by the reader 103 as being 'in heat' (as described previously in examples 1-5), a light, sound or other signal is brought to the attention of a gate operator who operates the drafting gate accordingly. This implementation eliminates the step of having a skilled farm worker for identifying and manually marking cows with, for example, shaving cream thus reducing the possibility of missing a cow 'in heat'. Furthermore there is no need to know the cow's ID as the cow is drafted immediately upon detection by the operator and hence expensive hardware is not required for the identification of cows. This system would work well in low-tech farms with small herd numbers and it would operate in both rotary as well as herringbone milking sheds.

The next level implementation is similar to the lowest level implementation described above but instead or additionally to having the tag reader 103 giving out a light or a sound when an 'in heat' cow is detected, the system also operates the gate through an actuator of some sort (e.g.: a hydraulic actuator). This replaces the skilled farm worker as well as the gate operator and two or three steps of the drafting process (i.e.: identifying, (marking) and operating the gate) is performed by the system automatically.

In a third implementation, the detection system of this invention is combined with either commercially available or specially developed farming systems to operate as part of a more integrated drafting system. Typically in this scenario, the tag reader 103 is not necessarily located at the exit race of the milking parlour. It is located anywhere before the exit together with a separate animal identification tag reader (e.g.: commercial RFID ear-tag reader). In this integrated drafting system, when the tag reader 103 of this invention picks up a cow as being 'in heat', the integrated system will store this information against the cow's ID that is read at the same time using the animal identification reader. When this cow passes through the exit gates, a second animal identification reader will read the cow's ID for second time. This ID is then compared to the list of stored IDs in the system and when a cow that has been marked as 'in heat' passes through the gate, the system would then operate the gate accordingly. This implementation replaces the skilled worker of prior art automated drafting systems that would normally identify and mark the cow for drafting by entering its ID into a database either manually or automatically by pressing a button. The gate operator is also replaced by the automated operation of the gate.

A further implementation of the drafting process (unrelated to the automated detection part of this invention) involves using an 'always-active' tag (as oppose to using the detection tags of examples 1-5 which are designed to indicate a status change when a cow is mounted) [Note that any of the previously described implementations can be carried out using these always-active tags in addition to using the detection tags of example 1-5]. The use of the 'always-active' tag is much simpler and cheaper than the detection tags of examples 1-5 as it does not include a flood coat layer(s), RF/EMF blocking circuit/loops, other activation devices, etc.

The basic principle of operation of this implementation involves a skilled farmer identifying an 'in heat' cow through any of the various prior art 'heat' detection methods as described previously in the background section (e.g.: tail paint, prior art scratchy indicator tags, visual observation). The skilled worker then attaches an always-active tag on the particular cow in-heat. The always-active tag incorporates means to attach them to animals e.g.: a sticker type tag, clip-on tag, Velcro type tag, a necklace or a tag having any other method of attachment to a cow. Furthermore the tags can be attached to the wool of a sheep, to the hide of a cow, or even be strapped to the leg or neck of an animal. Then the cow would be directed accordingly at the exit race of the milking parlour manually by a gate operator or automatically via a tag reader and a gate actuator as described above in the previous implementations.

EXAMPLE 7

Other Uses of the Tag

Although the preferred embodiments of the invention as described in examples 1-6, are used to detect the reproductive status of animals, there are a number of lower level uses for this technology.

This system also allows for the selection and/or detection of cows based on various different criteria and is not just limited to the detected of cows 'in heat'. Aspects of the invention also include the use of some or all of the apparatus of the detection system for selecting and/or drafting one or more cows having or showing any particular status or condition. The inventor has suggested, as examples, the use of the detection system for detecting/identifying cows with illness e.g.: mastitis, lameness, etc, for detecting/identifying cows to be moved to a different herd, for detecting/identifying cows under or over a particular age, of a particular breed or any other criteria, for detecting/identifying the lactation status of cows i.e.: drafting out dry cows, for detecting/identifying body condition score, etc.

In each of the above mentioned uses of the detection system the basic principle of operation of the system is the same. The system includes one or more 'always-active' tags, a tag reader and an interpretation module wherein the tags are attached to a cow/bull (or other animal) upon detection, by a farm worker, of a particular status or condition of the animal as mentioned above. Then the tag reader, preferably located at the exit race of a milking parlour, barn or feeding area, reads the tag giving out an audible, visual or other signal to a gate operator which drafts the animal accordingly or alternatively in an automated system the gate is operated automatically by the system. The signal can also be connected to an automated registration system, which simply records the event for later processing.

In the case of using the detection system for detecting/identifying illness in cows, for example mastitis, the presence of an active tag on the cow can be used to notify the farmer to withhold milk from that particular cow or in automated systems the milk from that particular cow could be diverted automatically to a separate holding tank once the tag reader detects a cow with the active tag attached or once a previously recorded cow is encountered.

Even though the system as described in examples 1-6 is in view of a detection system to be used on cows, the system would also work with other farm animals that needs to be drafted or selected based on any identifiable criterion e.g.: detection of body fat of sheep to be sent off to meat works The system can also function with the detection tags described in this invention in examples 1-5 and is not limited to the 'always-active' tags described previously. More specifically the detection system can be used to detect/indicate any particular condition or status of an animal using non-visual detection tags such as EAS tags or RFID tags and visual detection tags such as barcode tags. In the case of using the non-visual detection tags which indicate either an 'on' or 'off' status (e.g.: EAS tags), the system would only allow for one-way drafting, as a signal from the detection tags is either present or not.

In the case of using the system with non-visual/visual detection tags having a tag ID, which can indicate multiple conditions (e.g.: RFID or barcode tags), drafting in multiple directions is a possibility (i.e.: n-way drafting). In these detection tags, different encoded information can be stored, each indicating a different drafting destination. Typically these tags are also colour-coded (or any other indication type is used) so that a farm worker is able to readily identify them e.g.: a red marker is used for a cow in heat; a blue marker is used for a cow that needs veterinary attention and so on.

Furthermore the EAS tags mentioned above can also be used for drafting animals in multiple directions, by using a plurality of tags, each of which operating at a different frequency e.g.: no tag means no drafting of the animal, a tag operating at 8.5 MHz means draft animal to the left and a tag operating at 9.8 MHz means draft animal to the right and so on.

It should be noted that the terms RFID and EAS are used to describe various different types of electronic tags in the industry and sometimes the terms overlap the definition of each other as is explained later in the specification. However, in this example (example 7 only) the term RFID tag refers to a tag that holds and transmits information in numerical form (multiple bits of information stored). The term EAS tags refer tags which indicate either an 'on' or 'off' status (1-bit storage).

Advantages a) It is a cheap and efficient means of detecting the reproductive state of animals. Non-visual detection tags (e.g.: RFID, EAS) and readers are relatively cheap to manufacture and are easily sourced from a range of modern manufactures. It does not involve the use of any complex image capture devices or expensive software and hardware implementations which are usually required for prior art automated visual detection systems. The interpretation module is cheap to produce and could be installed on computer supplied by the farmer and/or integrated with existing farm automation systems. Furthermore the farmer does not have to observe the animals regularly as in prior art methods since the reading of the detection tags can be done automatically by a tag reader programmed to check the status of the tags at regular intervals. Therefore the detection system of this invention is more efficient than the prior art methods and missing the heat cycle of some animals is avoided.

b) The tags and the readers of this detection system is not sensitive to fouling, dust or dirt and is water proof and hence poor weather conditions or the rugged conditions of a farm does not effect its operation. This invention is not effected by these factors since it does not rely upon visual conditions such as 'line-of-sight', ambient lighting, precise positioning, etc usually required by prior art systems. Therefore a farmer does not miss the opportunity to take full advantage of the heat cycle of his/her animals saving time and money in selective breeding activities.

c) The non-visual detection (e.g.: RFID, EAS) tag system is more advantageous over the barcode tag system of example 5 since the non-visual detection tags does not require line of sight for scanning tags and are less susceptible to interference due to fouling.

d) The reading of the detection tags using a tag reader does not require the animals to be present at a specific location such as a milking shed of the farm. It can be performed at any location of the farm or outside using portable and handheld varieties of the detection tag readers available in the prior art.

e) The detection tags can be used to identify any particular state or condition of any animal and is not limited to detecting 'heat' of cows as described previously. Furthermore the preferred form of the tag is an EAS tag which is cheap and effective at indicating any state of an animal as a binary indication (i.e.: 1 or 0 indication).

f) The detection system of this invention can be incorporated into existing drafting processes of farms as described in example 6, which simplifies and reduces visual errors and costs involved in the drafting process.

Variations

The detection tags of this invention are preferably non-visual detection tags such as, for example, RFID or EAS tags and the tag readers used in this invention can be of any type used in the prior art. RFID and EAS tags are currently in wide use to detect (or identify) specific states as indicated by the tag and the same technology can be incorporated in this invention.

Electronic indicator tags/readers, commonly referred to as RFID tags/readers in the industry, are classified into several categories according to operational frequency. They are low frequency RFID (125 KHz, 134 KHz short range (0.5 m)) which is good for detecting water containing objects (i.e.: animals), high frequency RFID (13.65 Mhz. longer range (1 m)) which has an average ability to detect water/metal containing objects, ultra high frequency (860 to 930 MHz up to 3 m range) which is not good for detecting objects with water/metal and microwave RFID (2.45 to 5.8 Ghz limited range, expensive) which cannot be used for detecting water/metal containing objects. Therefore when using RFID detection systems, either a low or high frequency RFID tag/reader system is most suitable for use in this invention. However other systems can be used as desired in various other implementations.

Furthermore electronic article surveillance (EAS) tags/readers (sometimes referred to as identification tags, RFID tags or RF tags in the industry) are also classified into several categories according to there form of communication. The transmitter and the receiver of the EAS readers are sometimes combined into one single module but are usually found as two separate modules (e.g.: check-out gates at retail stores). Types of EAS tags/readers include magnetic (magneto-harmonic), acousto-magnetic (magnetostrictive), radio frequency and microwave EAS systems out of which radio frequency (RF) EAS systems are the most suitable type for the implementation of this invention. However implementations using other types of EAS tags are also possible.

For example, an implementation using magnetic/acousto-magnetic EAS tags involves the use of a tag which is physically damaged (completely or partially) during mounting action such that the tag is no longer detected by the reader. In an alternative implementation, the magnetic/acousto-magnetic EAS tags are shielded by a layer of magnetised paint which is removed during mounting action. In a further alternative, the status of the magnetic/acousto-magnetic tags can be made to be changed by attaching the mounting animal with a magnetising device which changes the state of the magnetic/acousto-magnetic tag secured on the female animal when mounted.

The interpretation module 105 disclosed in the specification can be installed as a software program on any type of computer including an embedded system as mentioned previously. It can be a laptop computer with a USB tag reader connected or a handheld device specifically made for interpreting the signal from the tag reader. It has a display to output whether the status of the scanned animal has changed or not. The results are preferably stored in a computer database and preferably the computer is integrated with or is part of existing farm automation systems.

As mentioned previously, the special blocking layer or conductive loop of the detection tag 101 is an RF/EMF blocking (or absorbing) flood coat layer 401 and/or RF/EMF blocking conductive circuit/loop 401a that is damaged or removed from the surface of the detection tags upon mounting of an animal. The RF/EMF blocking circuit/loop 401a of conductive material (round or otherwise) is preferably a ring of aluminium foil, an aluminium 'sticker' type (self-adhesive) ring, a painted-on ring of conductive paint, or a conductive liquid material contained circular tube or bladder. The ring 401a is either glued on to the tag (the ring being self-adhesive or otherwise), contained in a special pocket, sleeve of the tag or held on the top of the tag by ridges/rubber bands. It should be noted that the tag with the ring attached using special pockets, sleeves or ridges is relatively easier to manufacture in an automated and a more consistent way than a tag having a glued on/self-adhesive ring. Also the sticker-type (self-adhesive) ring was very prone to accidental breaking during trials. Therefore it is envisioned that the tag with the sleeve/pocket/rubber-band attachment of the ring, protects the ring from accidental breaking during use while still being able to be activated by a representative amount of rubbing.

The technique of using a circuit/loop of conductive material 401a blocks RF/EMF energy in a different method to that when using a flood coat layer 401 described previously. In this new method, the circuit/loop 401a forms an inductive loop when it experiences an RF/EMF field and hence it dissipates most of the energy in the RF/EMF field. Therefore it blocks the RF/EMF field from reaching the detection tag and prevents the tag from becoming activated. However once the circuit/loop 401a is broken partially or completely (i.e.: even a small cut in the aluminium foil or a tiny scratch through the conductive paint ring) the RF/EMF energy is no longer dissipated and the tag becomes readable by the tag reader. Therefore this technique does not require the removal of the entire flood coat layer to expose an antenna and only requires a break in the circuit/loop 401a (i.e.: only a small amount of conductive material needs to be displaced or removed). Once the circuit/loop 401a is broken, the conductive ring looses its ability to dissipate RF/EMF energy and is insufficient to block the RF/EMF field.

The above described technique of using a RF/EMF blocking circuit/loop 401a can be applied to any one of the above described examples 1-4 in combination with or without the flood coat layer 401. When using the RF/EMF blocking circuit/loop by itself the detection tags are shielded from the RF/EMF field of the tag reader while the loop is intact. A break in the circuit/loop is caused when a female animal (with the tag attached) is mounted by another animal as described previously.

It is important to note that, especially in relation to tags which use a RF/EMF blocking circuit/loop 401a, the use of a flood coat layer 401 is not essential and can be omitted from the tag for the purpose of electronic detection. The preferred option however is to include the flood coat layer 401 in the tag, as it enables a farmer to visually confirm the reproductive status of an animal as determined by the automated detection system of this invention (i.e.: if the flood coat layer 401 of a tag is rubbed off it visually indicates that the animal has been mounted).

Another method of providing visual confirmation to a farmer is to combine the current system of this invention with one of the prior art visual/manual detection systems e.g.: to use the tags of the current system along with tail paint on animals to confirm the reproductive status indicated by the tags. This proves to be an easy option to give the farmer some confidence and/or to identify accidental breaking of rings 401a of the tags from 'real-heat' indication.

Preferably the detection tags 101 disclosed in all examples of this specification are tapered at the edges to decrease chance of tag being removed during use (i.e.: when an animal is being mounted). All protective layers of the tags (405 and 411) are tapered as shown in the side-view diagram of FIG. 3.

Furthermore the bottom protective layer 405 of the tag is made thicker (for example by approximately 2 mm) at the centre of the tag as shown in the side-view diagram of FIG. 3. In the trials conducted by the inventor this was achieved by having a 2 mm foam sub-layer in the protective layer 405. The foam sub-layer can be omitted if the protective layer 405 is manufactured to have a centre thickness of 2 mm without the use of a foam layer. The thicker centre portion of the tags ensures a 2 mm separation between the electronic tag 403 and the animal skin resulting in an increased read-rate of the tags. Optionally the tag will be pre-shaped to follow the contours of the animal's back spine although this might not be necessary if the material of the protective layer 405 of the tag can be both thick and supple.

The layers of the detection tags 101 are not limited to the layers 401, 401a, 411, 403, 405, 407 and 409 as described and shown in FIGS. 3 and 4. Furthermore the layers may not necessarily be in the same order as disclosed in this specification and illustrated in the figures. In alternative embodiments of the invention, some layers may be omitted such as for example layers 411 and/or 407 and in further alternative embodiments, additional layers may be added to the tags as desired by various manufactures. For example, the adhesive layer 407 and peel off layer 409 may be omitted by some manufacturers and be replaced by special attachment layers which attaches the tags to animals using tag clips or special strings/rubber bands which tie the tags to the body of the animals. Other embodiments may exclude the protective lamination layers 411 and 405 and provide protection for the tag layer 403 by having other means such as plastic sleeves or pockets which secure the tags 403.

The tags 101 are attached to the animals using the adhesive layer 407 as described before. The adhesive layer 407 preferably comprises in a weather-proof adhesive. The preferred adhesive used by the inventor is known by the commercial name of 'Selleys Kwik Grip Spray' manufactured by Selleys Australia Ltd. It is known as an aerosol contact adhesive and is a water-resistant, heat-resistant (up to 70 degrees Celsius) solvent-based adhesive. It is fast drying and forms an instant bond on contact of two treated surfaces placed under pressure (i.e.: the skin of the animal and the adhesive layer 407). The adhesive dries clear and produces a durable bond on both adsorbent and non-absorbent surfaces. The adhesion of the tags to the animals can be greatly improved by applying the aerosol adhesive approximately 5 minutes prior to applying the tags which is especially useful when attaching the tags on to animals with wet/damp fur. The adhesive spray is made up of hexane isomers 30-60%, Naphtha (petroleum)-hydrotreated light (CAS number 64742-49-0) 30-60%, Heptane (CAS number 142-82-5) 10-30%, Acetone (CAS number 67-64-1) 1-<10%, n-Hexane (CAS number 110-54-3) 1-<5% and other minor adhesive ingredients. The composition of the suitable adhesive used in attaching the tags is given by way of example only, and various other types of adhesives having different compositions and/or other ingredients (non-aerosol or aerosol based) can also be used in alternative embodiments.

As mentioned in example 7, the technology developed for this invention can be used for purposes other than indicating the reproductive status of animals, such as the indicating of any other status of animals, for example health, identification data, growth rate, etc. In addition to these farming applications, the detection system is also applicable to other industries. These include using the tags in the packaging industry to indicate if an item (box, envelope or parcel) has been tampered with or opened (a tamper seal) and to identify a specific property of a packaged item by allowing an operator to manually activate one or more tags i.e.: a boxed product that can have various colours where the specific colour of the packaged product is identified by an operator that inserts the item in the box by activating the appropriate tag.

The terms 'RFID tags', 'EAS tags' and 'RFID/EAS tags' as used in this description includes all types of RFID/EAS type tags and all other existing electronic tag types available in the market. More particularly the term 'RFID tag' is not necessarily limited to tags which store identification data and also includes all types of RF tags which detects/identifies particular states of a tag (even if it does not store or send/receive identification data). Since the term 'RFID tags' is used in the industry to cover both RFID tags and RF tags and is more generally used to refer to any tag which uses radio frequency to indicate one or more states or conditions, it is used in the broadest possible sense of the term in this description.

Throughout the description of this specification, the words "identify" and "detect" (and their variations) are used interchangeably. Furthermore the terms 'detection tag', 'identification tag' are used interchangeably and is intended to broadly mean 'a tag' which indicates (i.e.: for detection/identifying purposes) any particular state(s) or condition of a tag as a '0' or '1' (or 'on/off') indication.

Throughout the description of this specification, the word "comprise" and variations of that word such as "comprising" and "comprises", are not intended to exclude other additives, components, integers or steps.

It will of course be realised that while the foregoing has been given by way of illustrative example of this invention, all such and other modifications and variations thereto as would be apparent to persons skilled in the art are deemed to fall within the broad scope and ambit of this invention as is hereinbefore described.

The invention claimed is:
1. A detection tag for detecting reproductive status of animals, the detection tag comprising:
an electronic signal transmitter;
a first surface that is affixable to an animal's hide; and
a second and opposite surface which includes abradable material capable of altering or preventing transmission of a signal transmitted by the electronic signal transmitter; and
wherein the detection tag is configured with the electronic signal transmitter underneath the abradable material such that removal of some or all of the abradable material alters the ability of the detection tag to transmit a signal electronically or alters a characteristic of the electronically transmitted signal,
wherein the abradable material includes a conductive circuit and the detection tag is configured such that partial or complete removal of the conductive circuit, or breaking of the conductive circuit, allows electronic transmission of status information from the detection tag, and
wherein the conductive circuit is an RF/EMF blocking circuit/loop made from a conductive material, and the circuit/loop shields electronic components of the detection tag from RF/EMF energy by forming an inductive loop.

2. A detection tag as claimed in claim 1, wherein the abradable material is a removable flood coat layer, and removal of the flood coat layer of the second surface of the detection tag allows or disallows electronic transmission of status information from the detection tag.

3. A detection tag as claimed in claim 2, wherein the flood coat layer covers part or all of an antenna of the detection tag.

4. A detection tag as claimed in claim 3, wherein removal of part or all of the flood coat layer alters a strength and/or frequency of the signal from the detection tag.

5. A detection tag as claimed in claim 2, wherein the flood coat layer includes a layer of conductive material or RF/EMF shielding or absorbing material.

6. A detection tag as claimed in claim 2, wherein the flood coat layer includes a plurality of layers, and at least one of the layers is a layer of RF/EMF shielding/blocking material and at least one of the layers is a layer of latex material.

7. A detection tag as claimed in claim 1, wherein the conductive circuit of the detection tag is configured such that it is damaged or broken partially or completely when a first animal is mounted by a second animal.

8. A detection tag as claimed in claim 1, wherein the abradable material forms, or is at least a part of, an antenna of the electronic signal transmitter.

9. A detection tag as claimed in claim 1, wherein the detection tag is normally inactive and is activated only when the abradable material is partially or completely removed.

10. A detection tag as claimed in claim 1, wherein the detection tag incorporates a 'Radio Frequency Identification' (RFID) electronic circuit/micro chip or an 'Electronic Article Surveillance' (EAS) electronic circuit/micro chip.

11. A detection tag as claimed in claim 10, wherein the RFID circuit/chip uses low or high frequency radio frequency (RF) communication.

12. A detection tag as claimed in claim 10, wherein the EAS electronic circuit or micro chip uses radio frequency (RF), magnetic (magneto-harmonic), acousto-magnetic (magnetostrictive) or microwave communication.

13. A detection tag as claimed in claim 1, wherein the altered characteristic of the electronically transmitted signal is a change in the frequency range within which the detection tag becomes readable.

14. A detection tag as claimed in claim 1, wherein the detection tag is thicker in regions of the tag covered by the abradable material.

15. A detection tag as claimed claim 1, wherein the detection tag includes an adhesive layer on the first surface.

16. A detection tag as claimed in claim 1, wherein the detection tag is substantially bone-shaped with two wing portions flanking a central portion, the wing portions being wider than the central portion.

17. A detection tag as claimed in claim 1, wherein the conductive material is selected from the group consisting of aluminium foil, conductive paint, liquid conductive material, and combinations thereof.

18. An apparatus for detecting a reproductive status of an animal, wherein the apparatus includes at least one detection tag as claimed in claim 1 and at least one tag reading device and/or interpretation module which is configured to interpret the signal from the detection tag.

19. A method of detecting a reproductive state of an animal wherein the method comprises the steps of:
   affixing a detection tag onto a female animal, wherein the detection tag comprises:
      an electronic signal transmitter;
      a first surface that is affixable to the female animal's hide; and
      a second and opposite surface which includes abradable material capable of altering or preventing transmission of a signal transmitted by the electronic signal transmitter; and
      wherein the detection tag is configured with the electronic signal transmitter underneath the abradable material such that removal of some or all of the abradable material alters the ability of the detection tag to transmit a signal electronically or alters a characteristic of the electronically transmitted signal,
   allowing the female animal to mingle with other animals for a period of time,
   causing potential removal of some or all of the abradable material on the detection tag by permitting the female animal to be mounted by another animal,
   passing the female animal by a detection tag reading device or taking the detection tag reading device to the female animal, and
   evaluating the signal, or absence of the signal, from the detection tag, and making a determination as to the reproductive state of the female animal.

20. A detection tag for detecting reproductive status of animals, the detection tag comprising:
   an electronic signal transmitter;
   a first surface that is affixable to an animal's hide; and
   a second and opposite surface which includes abradable material capable of altering or preventing transmission of a signal transmitted by the electronic signal transmitter; and
   wherein the detection tag is configured with the electronic signal transmitter underneath the abradable material such that removal of some or all of the abradable material alters the ability of the detection tag to transmit a signal electronically or alters a characteristic of the electronically transmitted signal,
   wherein the abradable material is a removable flood coat layer, and removal of the flood coat layer of the second surface of the detection tag allows or disallows electronic transmission of status information from the detection tag,
   wherein the flood coat layer includes a plurality of layers, and at least one of the layers is a layer of RF/EMF shielding/blocking material and at least one of the layers is a layer of latex material.

* * * * *